(12) United States Patent
Space et al.

(10) Patent No.: US 12,371,170 B2
(45) Date of Patent: Jul. 29, 2025

(54) VENTILATION SYSTEMS AND METHODS FOR INTERNAL CABINS OF VEHICLES

(71) Applicant: THE BOEING COMPANY, Chicago, IL (US)

(72) Inventors: David R. Space, Everett, WA (US); Stephen M. Trent, Everett, WA (US); Stephanie K. Licht, Everett, WA (US); Timothy J. Arnaud, Everett, WA (US); James A. Fullerton, Bothell, WA (US)

(73) Assignee: The Boeing Compnay, Chicago, IL (US)

( * ) Notice: Subject to any disclaimer, the term of this patent is extended or adjusted under 35 U.S.C. 154(b) by 515 days.

(21) Appl. No.: 17/496,904

(22) Filed: Oct. 8, 2021

(65) Prior Publication Data
US 2022/0135235 A1     May 5, 2022

Related U.S. Application Data

(60) Provisional application No. 63/106,917, filed on Oct. 29, 2020.

(51) Int. Cl.
*B64D 13/06* (2006.01)
*A61L 9/20* (2006.01)
*B64D 11/06* (2006.01)

(52) U.S. Cl.
CPC ............... *B64D 13/06* (2013.01); *A61L 9/20* (2013.01); *B64D 11/0626* (2014.12);
(Continued)

(58) Field of Classification Search
CPC .... B64D 13/06; B64D 13/00; B64D 11/0626; B64D 2013/064; B64D 2013/0651; B64D 2013/003; B64D 2013/0662; A61L 9/20; A61L 2209/12; A61L 2209/14; F24F 8/22; F24F 13/0604; Y02T 50/50
(Continued)

(56) References Cited

U.S. PATENT DOCUMENTS 5,795,018 A    8/1998  Schumacher
9,889,939 B2   2/2018  Zhang
(Continued)

FOREIGN PATENT DOCUMENTS

CN   105292493 B  *  4/2018
DE   19830797        10/2007
(Continued)

OTHER PUBLICATIONS

Extended European Search Report for EP 21204931.6-1010, dated Mar. 9, 2022.
Communication re EP 21204931.6-10104 dated Sep. 18, 2024.

*Primary Examiner* — Steven B McAllister
*Assistant Examiner* — Charles R Brawner
(74) *Attorney, Agent, or Firm* — Joseph M. Butscher; The Small Patent Law Group LLC

(57) ABSTRACT

A system and method include a seat assembly including a seat duct fluidly coupled to one or more air outlets. An air delivery manifold is underneath the seat assembly. The air delivery manifold includes a first outlet port. The seat duct is fluidly coupled to the first outlet port. Air is delivered to the one or more air outlets via the air delivery manifold.

20 Claims, 8 Drawing Sheets

(52) U.S. Cl.
CPC ....... *A61L 2209/12* (2013.01); *A61L 2209/14* (2013.01); *B64D 2013/064* (2013.01); *B64D 2013/0651* (2013.01)

(58) Field of Classification Search
USPC ........................................................ 454/136
See application file for complete search history.

(56) References Cited

U.S. PATENT DOCUMENTS

| | | | |
|---|---|---|---|
| 10,029,797 | B2 | 7/2018 | Space |
| 2008/0053126 | A1* | 3/2008 | Ebigt ................. B60N 2/5657 62/237 |
| 2009/0104868 | A1* | 4/2009 | Sanchez ................ F24F 13/082 454/367 |
| 2010/0043794 | A1 | 2/2010 | Saito |
| 2010/0081369 | A1 | 4/2010 | Space |
| 2013/0327891 | A1* | 12/2013 | Zhang ................... B64D 13/08 244/118.5 |
| 2014/0179212 | A1* | 6/2014 | Space ................. B60N 2/5635 454/76 |
| 2015/0099445 | A1* | 4/2015 | Ashburn ............ B60H 1/00285 454/152 |
| 2016/0101869 | A1 | 4/2016 | Markwart |
| 2019/0047449 | A1* | 2/2019 | Fujii .................... B60N 2/5657 |
| 2021/0309373 | A1* | 10/2021 | Le Cam .............. B60N 2/5678 |
| 2021/0318008 | A1* | 10/2021 | Szoradi .................... F24F 11/56 |
| 2021/0325064 | A1* | 10/2021 | Amhamed ......... B01D 53/0415 |
| 2021/0370212 | A1* | 12/2021 | Misawa ............. B64D 11/0626 |
| 2021/0387731 | A1* | 12/2021 | Cordatos .................... A61L 9/20 |
| 2021/0393820 | A1* | 12/2021 | Childress ............... B64D 11/06 |

FOREIGN PATENT DOCUMENTS

| | | |
|---|---|---|
| EP | 2310264 | 9/2012 |
| EP | 3805665 | 4/2021 |
| EP | 3922557 | 12/2021 |
| EP | 3925880 | 12/2021 |
| JP | H10109644 | 4/1998 |

\* cited by examiner

VENTILATION SYSTEMS AND METHODS FOR INTERNAL CABINS OF VEHICLES

CROSS-REFERENCE TO RELATED APPLICATIONS

This application relates to and claims priority benefits from U.S. Provisional Application No. 63/106,917, entitled "Ventilation Systems and Methods for Internal Cabins of Vehicles," filed Oct. 29, 2020, which is hereby incorporated by reference in its entirety.

FIELD OF THE DISCLOSURE

Embodiments of the subject disclosure generally relate to ventilation systems and methods for internal cabins of vehicle, such as commercial aircraft.

BACKGROUND OF THE DISCLOSURE

Vehicles such as commercial aircraft are used to transport passengers between various locations. Many commercial vehicles such as aircraft have High Efficiency Particulate Air (HEPA) filters in air conditioning systems that are able to entrap microbes and pathogens. The HEPA filters receive and clean air exiting the cabin or about to enter the cabin. HEPA filters and frequent cleaning of the cabin between flights are some methods to ensure the health of the passengers and crew onboard the aircraft.

Further, certain passengers may prefer to wear masks within an internal cabin of a vehicle in order to reduce the risk of spreading pathogens. However, wearing masks during long flights, for example, may be uncomfortable for certain passengers.

SUMMARY OF THE DISCLOSURE

A need exists for a system and a method for preventing, minimizing, or otherwise reducing the spread of pathogens between passengers onboard a vehicle during a trip, such as between passengers in an internal cabin of an aircraft during a flight, without risking harm to the passengers.

With that need in mind, certain embodiments of the subject disclosure provide a system including a seat assembly having a seat duct fluidly coupled to one or more air outlets, and an air delivery manifold underneath the seat assembly. The air delivery manifold includes a first outlet port. The seat duct is fluidly coupled to the first outlet port. Air is delivered to the one or more air outlets via the air delivery manifold.

In at least one embodiment, the air delivery manifold is below a floor, and the seat assembly is supported on a top surface of the floor.

In at least one embodiment, an air supply receives the air. A supply duct is fluidly coupled to the air supply and the air delivery manifold. The air is drawn into the supply duct from the air supply and provided to the air delivery manifold from the supply duct.

In at least one embodiment, one or more fans are disposed within the supply duct.

In at least one embodiment, an air conditioning sub-system is disposed on or within the supply duct upstream from the air delivery manifold. For example, the air conditioning sub-system includes one or more heaters, one or more filters, or one or more humidifiers.

In at least one embodiment, an ultraviolet (UV) disinfection sub-system is disposed on or within the supply duct upstream from the air delivery manifold. The UV disinfection sub-system includes one or more UV light emitters configured to emit UV light into the air.

In at least one embodiment, the air delivery manifold further includes a second outlet port. The second outlet port can be open and configured to provide the air into an internal cabin. Optionally, the second outlet port can be plugged.

In at least one embodiment, at least a portion of the seat duct extends into at least a portion of one or both of a backrest or a headrest of the seat assembly. In at least one example, the headrest includes the one or more air outlets.

In at least one embodiment, one or more return air grills are above the seat assembly. The air is upwardly drawn from a breathing space associated with the seat assembly into the one or more return air grills. As an example, the one or more return air grills are disposed within a ceiling of an internal cabin.

In at least one embodiment, the seat duct is removably coupled to the first outlet port.

Certain embodiments of the subject disclosure provide a method including fluidly coupling a seat duct of a seat assembly to a first outlet port of an air delivery manifold underneath the seat assembly, and delivering air to one or more air outlets of the seat assembly via the air delivery manifold.

Certain embodiments of the subject disclosure provide a vehicle including an interior cabin including a floor, and a seat assembly supported on a top surface of the floor within the interior cabin. The seat assembly includes a seat duct fluidly coupled to one or more air outlets. An air delivery manifold is below the floor underneath the seat assembly. The air delivery manifold includes a first outlet port. The seat duct is fluidly coupled to the first outlet port. Air is delivered to the one or more air outlets via the air delivery manifold.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the subject disclosure provide a displacement ventilation system having one or more conduits (such as ducts, plenums, pipes, tubes, manifolds, and/or the like) below a floor of an internal cabin of a vehicle. Airflow is distributed upwardly from the conduits into ducts within seat assemblies supported above the floor. The seat assemblies also include one or more air outlets, such as personal ventilation nozzles within a headrest, that direct air toward a breathing zone (for example, a volume of space in and around the headrest where a passenger breathes). Return air can then be drawn into return air grills such as in the ceiling, upper portions of an internal cabin, and/or the like). The return air can be treated and recirculated within the internal cabin, or exhausted out of the vehicle. In at least one embodiment, air flows in a bottom-up direction, and can provide a plug air flow system.

The ventilation system having air outlets in a seat assembly (for example, each seat assembly within an internal cabin) removes exhaled air, including any pathogens, from a breathing space, and draws such exhaled air away from the passengers within the internal cabin. As such, embodiments of the present disclosure provide systems and methods that reduce the spread of pathogens within an internal cabin, as well as provide efficient airflow within internal cabin.

As noted, in at least one embodiment, the conduits are below the floor of the internal cabin. The ducts of the seat assemblies couple to the conduits from above the conduits. In this manner, conduits need not be disposed within sidewalls, as the airflow is directed from a bottom-up direction, in contrast to a top-down direction. Because less air conduits can be used, the manufacturing process for the vehicle is less extensive, less time consuming, and less costly. Further, by reducing an amount of conduits within the vehicle (such as less or nor conduits within side wall portions), the vehicle is lighter, and consequently more fuel efficient.

Figure 1:
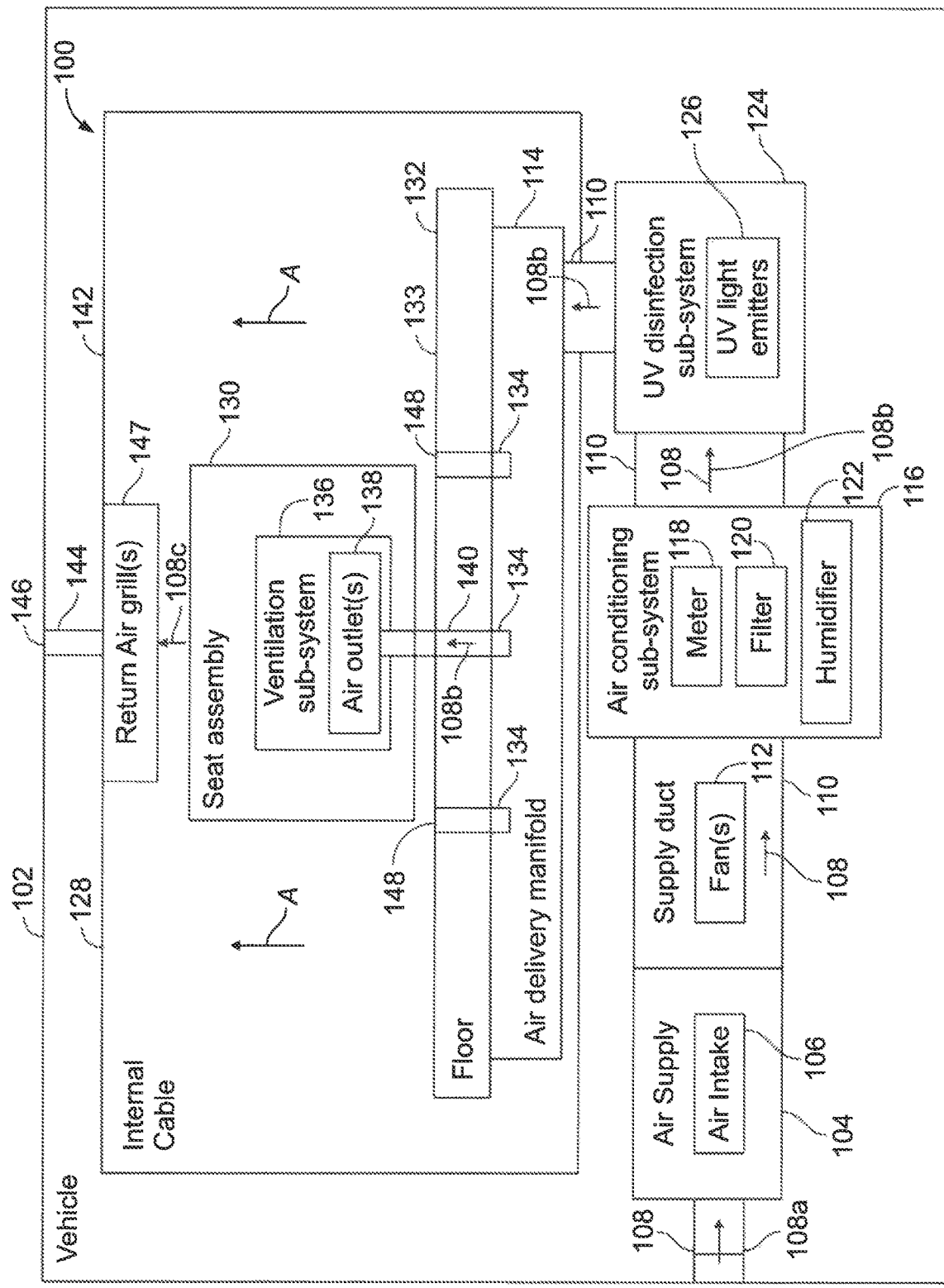
FIG. 1 illustrates a schematic diagram of an air distribution system for a vehicle, according to an embodiment of the subject disclosure.

FIG. 1 illustrates a schematic diagram of an air distribution system 100 for a vehicle 102, according to an embodiment of the subject disclosure. The air distribution system 100 includes an air supply 104 having an air intake 106 that receives air 108 from outside the vehicle 102 (that is, external air). For example, the air intake 106 draws outside air into the vehicle 102 via the air intake 106. In at least one example, the vehicle 102 is an aircraft, and the air supply 104 includes one or more air conditioners that receive bleed air from one or more engine of the aircraft. As another example, the air supply 104 includes one or more fans, pumps, and/or the like that draw the air 108 into the vehicle 102.

The air intake 106 of the air supply 104 receives the air 108 from outside the vehicle 102. The air 108 is then drawn into a supply duct 110. In at least one embodiment, the supply duct 110 includes one or more fans 112 that draw the air 108 away from the air intake toward an into an air delivery manifold 114.

In at least one embodiment, an air conditioning sub-system 116 is disposed on and/or within the supply duct 110, upstream from the air delivery manifold 114. The air conditioning sub-system 116 is configured to condition the air 108 that is drawn into the supply duct 110. For example, the air conditioning sub-system 116 includes one or more heaters 118 (such as heat exchangers, heating coils, and/or the like) that heat the air 108, one or more filters 120 (such as HEPA filters, sorbent materials, activated charcoal materials, and/or the like) that filter impurities from the air 108, and/or one or more humidifiers 122 that regulate the humidity of the air 108. Additionally or alternatively, the air conditioning sub-system 116 can include a dehumidifier. Optionally, the air conditioning sub-system 116 can include less than all of the heater 118, the filter 120, and/or the humidifier 122. Alternatively, the air conditioning sub-system 116 may not be disposed within the supply duct 110.

In at least one embodiment, an ultraviolet (UV) disinfection sub-system 124 is disposed on and/or within the supply duct 110 upstream from the air delivery manifold 114. The UV disinfection sub-system 124 can be downstream (or optionally, upstream) from the air conditioning sub-system 116. The UV disinfection sub-system 124 includes one or more UV light emitters 126 (such as one or more UV lamps, bulbs, light emitting diodes (LEDs), and/or the like) that are configured to emit UV light into the air 108 to disinfect the air 108. In at least one embodiment, the UV light emitters 126 are configured to emit UV light in the far UV spectrum, such as between 220-230 nanometers (nm). For example, the UV light emitters 126 can be configured to emit UV light at a wavelength of 222 nm. In at least one other embodiment, the UV light emitters 126 are configured to emit UV light in the UVC spectrum, such as between 230-280 nm. For example, the UV light emitters 126 can be configured to emit UV light at a wavelength of 254 nm. Optionally, the UV light emitters 126 can be configured to emit UV light at different wavelengths, such as within the far UV spectrum and the UVC spectrum. As another option, the UV light emitters 126 can be configured to emit UV light at wavelengths other than within the far UV spectrum or the UVC spectrum. Alternatively, the UV disinfection sub-system 124 is not disposed on and/or within the supply duct 110.

The UV disinfection sub-system 124 is configured to neutralize pathogens within air traveling through the supply duct 110. The UV light emitters 126 are disposed along a length of the supply duct 110 to ensure that pathogens (such as bacteria, viruses, germs, and the like) that may be within the air passing through the supply duct 110 are neutralized (for example, killed) before entering the air delivery manifold 124.

The supply duct 110 is in fluid communication with the air delivery manifold 114. For example, the supply duct 110 is connected to the air delivery manifold 114, such as through one or more fluid couplings. As another example, the delivery manifold 114 is an extension of the supply duct 110. The air delivery manifold 114 extends over a portion of an internal cabin 128 of the vehicle 102, such as under and across a row of seat assemblies 130. In at least one embodiment, multiple air delivery manifolds 114 are disposed within the internal cabin 128 and in communication with the supply duct 110. For example, each air delivery manifold 114 can be directly coupled to the supply duct 110. As another example, the air delivery manifolds 114 can be fluidly coupled together through connection ducts, and less than all of the air delivery manifolds 114 are directly coupled to the supply duct 110 (for example, one air delivery manifold 114 is directly coupled to the supply duct 110, with downstream air delivery manifolds 114 coupled together through connection ducts).

The air delivery manifold 114 is disposed below a floor 132 of the internal cabin 128. A seat assembly 130 is supported above the floor 132, opposite from the air delivery manifold 114. As described herein, the seat assembly 130 includes a seat duct 140 that is configured to fluidly couple to an outlet port 134 of an air delivery manifold 114, which can be disposed below the floor 132.

The air delivery manifold 114 includes a plurality of outlet ports 134. The outlet ports 134 allow the air 108 to pass out of the air delivery manifold 114.

The seat assembly 130 includes a ventilation sub-system 136 having one or more air outlets 138 in fluid communication with a seat duct 140 that fluidly couples to an outlet port 134 of the air delivery manifold 114. The seat duct 140 is formed on and/or within at least a portion of the seat assembly 130. The seat assembly 130 includes the seat duct 140. For example, the seat duct 140 extends through a backrest and/or headrest of the seat assembly 130. As another example, at least a portion of the seat duct 140 is disposed over (such as on a rear surface, a side surface, or the like) of the backrest, the headrest, armrest(s), seat pan, and/or the like of the seat assembly 130.

As an example, the air outlets 138 can be formed in the headrest. In at least one embodiment, the air outlets 138 are part of distribution nozzles formed in the headrest. The air outlets 138 are configured to deliver the air 108 to a breathing space proximate the seat assembly 130. The breathing space is a volume that includes the headrest and areas in which a passenger seated on the seat assembly inhales the air and exhales air. As one example, the breathing space is a spherical volume of space extending 2 feet or less from the headrest in all directions.

In at least one embodiment, one or more return air grills 147 are disposed within the internal cabin 128. For example, the return air grills 147 are disposed within a ceiling 142 (which may include bottoms of stowage bin assemblies) of the internal cabin 128. The return air grills 147 can include one or more fans that upwardly draw air into the return air grills 147. Optionally, the fans can be disposed within conduits, ducts, or the like downstream from the return air grills 147. Optionally, the return air grills 147 are disposed within upper portions of side walls. The return air grills 147 are in fluid communication with a return duct 144 that is in fluid communication with an exhaust opening 146 of the vehicle 102. Alternatively, the return duct 144 is in fluid communication with a recirculation duct that is also in fluid communication with the air supply 104, for example.

In operation, the air supply 104 draws in external air 108a into the supply duct 110. The fan(s) 112 operate to draw the external air 108a into and through the air conditioning sub-system 116. The air conditioning sub-system 116 treats the external air 108a to provide treated air 108b. For example, the heater 118 can heat the external air 108a. As another example, the filter 120 can filter particulate matter and impurities from the external air 108a. As another example, the humidifier 122 can humidify the external air 108a.

The treated air 108b can also be treated by the UV disinfection sub-system 124, which can be downstream (or optionally, upstream) from the air conditioning sub-system 116. The UV light emitters 126 of the UV disinfection sub-system 124 emit UV light into the air 108 to neutralize pathogens (such as bacteria, germs, viruses, and/or the like).

The air conditioning sub-system 116 and the UV disinfection sub-system 124 treat the external air 108a to provide the treated air 108b to the air delivery manifold 114. That is, the air is treated, such as via the air conditioning sub-system 116 and/or the UV disinfection sub-system 124, prior to being delivered to the seat assembly 130 via the air delivery manifold 114.

As shown, the air distribution system 100 includes an air conditioning sub-system 116 and the UV disinfection sub-system 124 that are upstream from the seat assembly 130 within the internal cabin 128. As such, the seat assembly 130 need not include separate air conditioning components, such as heaters, filters, humidifiers, UV light emitters, and/or the like. In this manner, the seat assembly 130 is able to provide clean, purified, sanitized air to a breathing space without the complexity and costs associated with having separate and distinct air conditioning components and UV light emitters. Alternatively, the seat assembly 130 can include one or more air conditioning components and/or UV light emitters that can be individually controlled.

The fan(s) 112 direct the treated air 108b into the air delivery manifold 114 and the seat assembly 130. The fans 112 may be disposed throughout the supply duct 110. For example, the fans 112 can be upstream and/or downstream from the air conditioning sub-system 116 and the UV disinfection light sub-system 124. In at least one embodiment, one or more fans 112 can also be disposed within the air delivery manifold 114. The fans 112 direct airflow into the seat assembly 130. Accordingly, the seat assembly 130 need not include separate fans, which reduces cost, complexity, and weight of the seat assembly 130. By reducing the number of components within the seat assembly 130 (such as air conditioning components, UV light emitters, fans, and/or the like), the weight of the seat assembly 130 is reduced. Lighter seat assemblies 130 onboard a vehicle 102 lead to increased fuel efficiency. Alternatively, the seat assembly 130 can include one or more fans.

The treated air 108b passes into the seat duct 140, which is fluidly coupled to an outlet port 134 of the air delivery manifold 114. The treated air 108b is then delivered to the breathing space associated with the seat assembly 130 through the air outlets 138, such as may be on or within the headrest, backrest, and/or the like of the seat assembly 130. A passenger seated on the seat assembly 130 inhales the clean, purified, treated air 108b, and exhales exhaled air 108c into the breathing space. The exhaled air 108c is drawn away from the breathing space (and away from other passengers within the internal cabin 128) by the airflow A, which is in a bottom-up direction. The exhaled air 108c is drawn into the return air grills 147, and into the return duct 144. The exhaled air 108c can then be exhausted out of the vehicle 102 through the exhaust opening 146, or recirculated to the air supply 104, such as through a recirculation duct.

In at least one embodiment, the internal cabin 128 includes a plurality of seat assemblies 130 having ventilation sub-systems 136 fluidly coupled to one or more air delivery manifolds 114, which, in turn, are fluidly coupled to the supply duct 110. In at least one embodiment, all of the seat assemblies 130 within the internal cabin 128 are fluidly coupled to one or more air delivery manifolds 114. In at least one other embodiment, less than all of the seat assemblies 130 within the internal cabin 128 are fluidly coupled to one or more air delivery manifolds 114.

In at least one embodiment, the air delivery manifold 114 includes a plurality of outlet ports 134. Some of the outlet ports 134 are in fluid communication with seat ducts 140 of seat assemblies 130. Other outlet ports 134 can be opened and fluidly coupled to air outlets 148 formed in the floor 132, thereby providing the treated air 108b into the internal cabin 128, in general, as well as to the air outlets 138 of the seat assemblies 130. In at least one other embodiment, at least some of the outlet ports 134 that are not coupled to seat ducts 140 can be plugged to prevent fluid passage therethrough. The outlet ports 134 can be plugged to control air pressure of the treated air 108b that is delivered to the seat assemblies 130.

As described herein, in at least one embodiment, the system 100 includes the seat assembly 130 having the seat duct 140 fluidly coupled to the one or more air outlet 138. The air delivery manifold 114 is underneath the seat assembly 130. As an example, the air delivery manifold 114 is not part of the seat assembly 130. The air delivery manifold 114 includes the outlet port 134. The seat duct 140 is fluidly coupled to the outlet port 134. Air (such as the treated air 108b) is delivered to the one or more air outlets 138 via the air delivery manifold 114.

In at least one embodiment, the air delivery manifold 114 is below the floor 132. Optionally, the air delivery manifold 114 can be embedded within the floor 132, or have at least a portion above the floor 132. The seat assembly 130 is supported on a top surface 133 of the floor 132.

Figure 2:
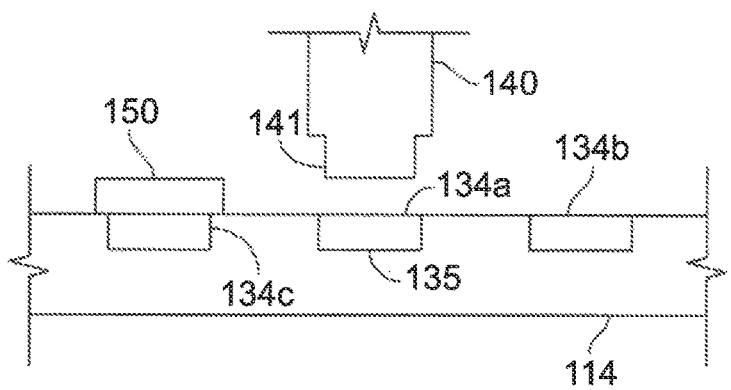
FIG. 2 illustrates a schematic diagram of a seat duct separated from an outlet port of an air delivery manifold, according to an embodiment of the subject disclosure.

FIG. 2 illustrates a schematic diagram of a seat duct 140 separated from an outlet port 134a of the air delivery manifold 114, according to an embodiment of the subject disclosure. Referring to FIGS. 1 and 2, the seat assembly 130 includes the seat duct 140 that is configured to fluidly couple with the outlet port 134a. For example, the seat duct 140 can include a plug 141 that is configured to mate with a reciprocal socket 135 of the outlet port 134a. Optionally, the seat duct 140 can include the socket, and the outlet port 134a can include the plug. In this manner, the seat duct 140 can removably couple to the outlet port 134a through a plug and socket connection. In at least one other embodiment, the seat duct 140 can removably couple to the outlet port 134a through one or more latches, a threadable connection, one or more clasps, one or more latches, and/or the like. By removably coupling the seat duct 140 to the outlet port 134a, the seat assembly 130 can be selectively removed and replaced, such as if the seat assembly 130a is in need of maintenance. In at least one other embodiment, the seat duct 140 can couple to the outlet port 134 through one or more fasteners, such as screws, bolts, or the like. In at least one other embodiment, the seat duct 140 can be permanently fixed to the outlet port 134a, such as through welding, bonding, or the like.

As shown, the outlet port 134b can be open, thereby providing the treated air 108b to the internal cabin 128, such as to an aisle between seat assemblies 130. The outlet port 134c can be closed, such as via a plug 150 that is removably coupled to the outlet port 134c.

Each seat assembly 130 within the internal cabin 128 can fluidly couple to a respective outlet port 134 through a respective seat duct 140. That is, each seat assembly 130 can include a seat duct 140 that fluidly couples to a respective outlet port 134. Optionally, a plurality of seat assemblies 130 can fluidly couple to an outlet port 134 through a common seat duct.

Figure 3:
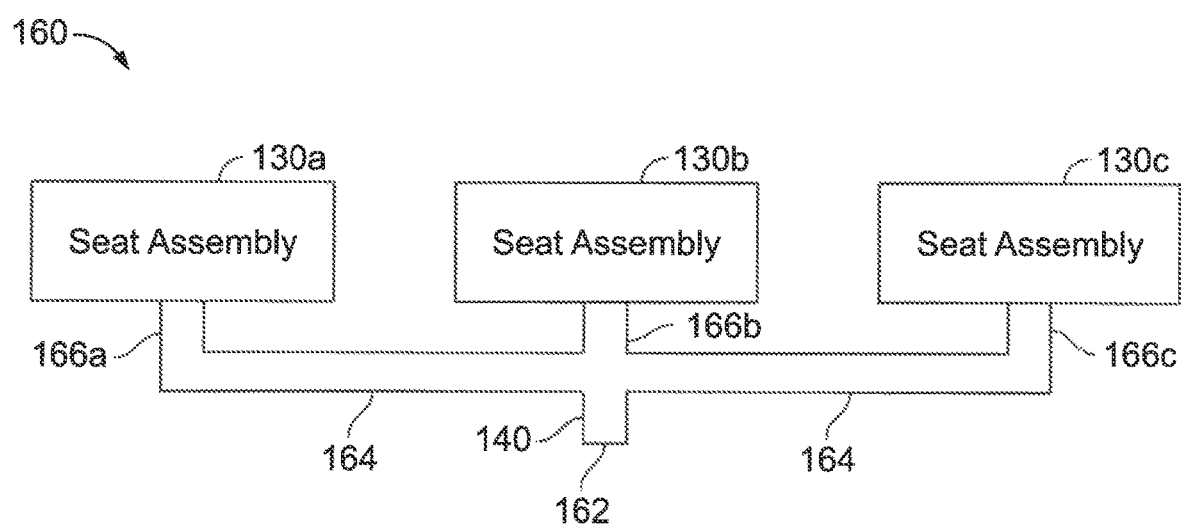
FIG. 3 illustrates a schematic diagram of a seat system, according to an embodiment of the subject disclosure.

FIG. 3 illustrates a schematic diagram of a seat system 160, according to an embodiment of the present disclosure. The seat system 160 includes a plurality of seat assemblies 130a, 130b, and 130c. The seat system 160 can include more or less seat assemblies than shown.

The seat system 160 includes a seat duct 140 that is common to the seat assemblies 130a, 130b, and 130c. For example, the seat duct 140 includes an air inlet 162 that is configured to fluidly couple to an outlet port 134 of the air delivery manifold 114 (shown in FIGS. 1 and 2). The air inlet 162 fluidly connects to a branching duct 164 having delivery ducts 166a, 166b, and 166c that fluidly coupled to the air outlets 138 (shown in FIG. 1) of the respective seat assemblies 130a, 130b, and 130c.

Figure 4:
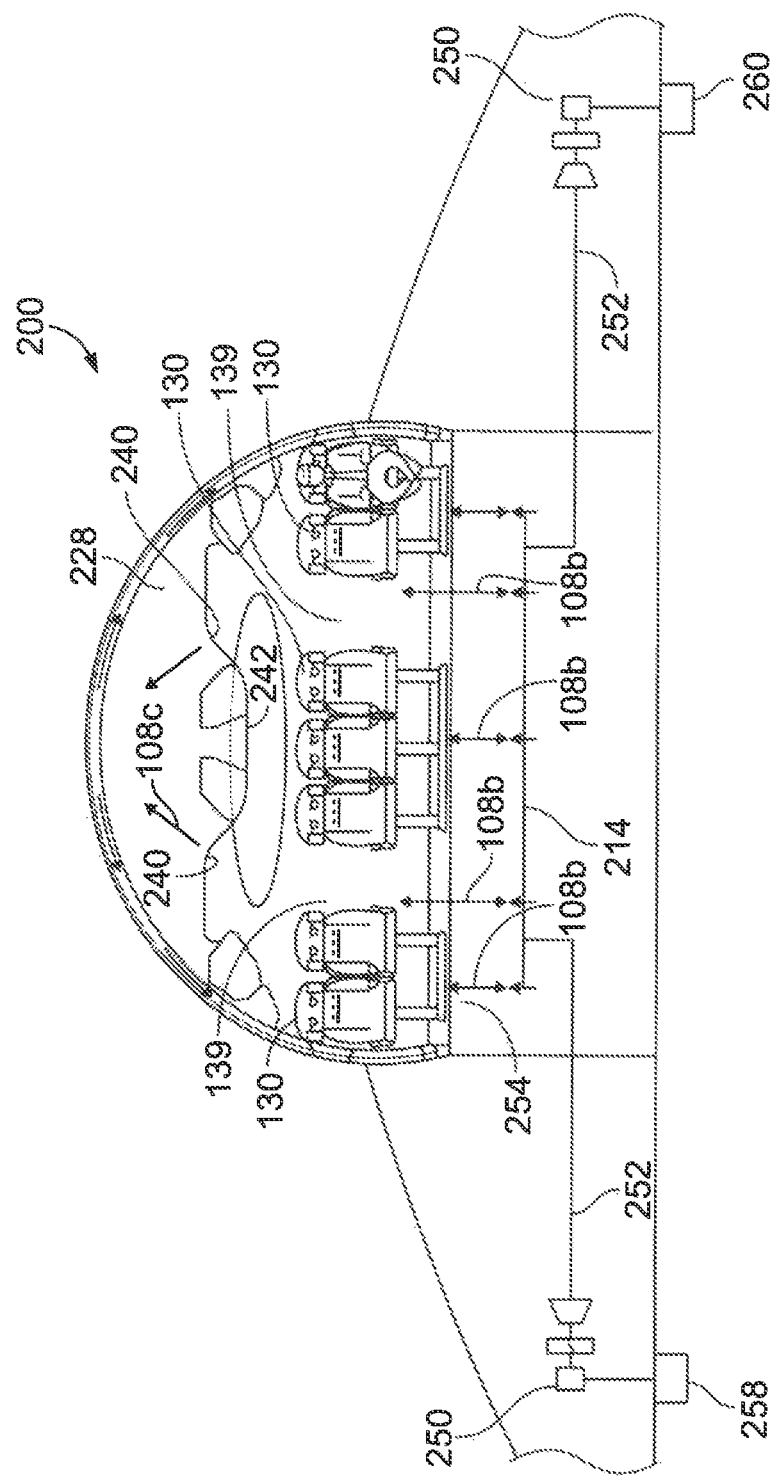
FIG. 4 illustrates a schematic diagram of an aircraft, according to an embodiment of the subject disclosure.

FIG. 4 illustrates a schematic diagram of an aircraft 200, according to an embodiment of the subject disclosure. The aircraft 200 is an example of the vehicle 102, shown and described with respect to FIG. 1. An air supply device 250 (an example of the air supply 114 shown in FIG. 1) is fluidly coupled to a supply duct 252 (an example of the supply duct 110 shown in FIG. 1), which, in turn, is fluidly coupled to an air delivery manifold 214 (an example of the air delivery manifold 114 shown in FIG. 1). A flow control device such as, but not limited to, a valve, can be coupled in flow communication with supply duct 252 and positioned in between air supply device 250 and air supply outlet 254. In the illustrated example, the air supply device 250 is shown coupled to a first engine 258 and a second engine 260, for example a right engine and a left engine respectively. The air supply device 250 can be coupled to a single engine or more than two engines. The air supply device 250 can also be coupled to a compressor (not shown) to bleed air from fuselage without flow communication with engines 258 and 260.

As shown, treated air 108b is provided to the seat assemblies 130 and, optionally, to aisles 139 and/or other areas within the internal cabin 228. Exhaled air 108c can be drawn into the return air grills 240, such as may be disposed within a ceiling 242.

Figure 5:
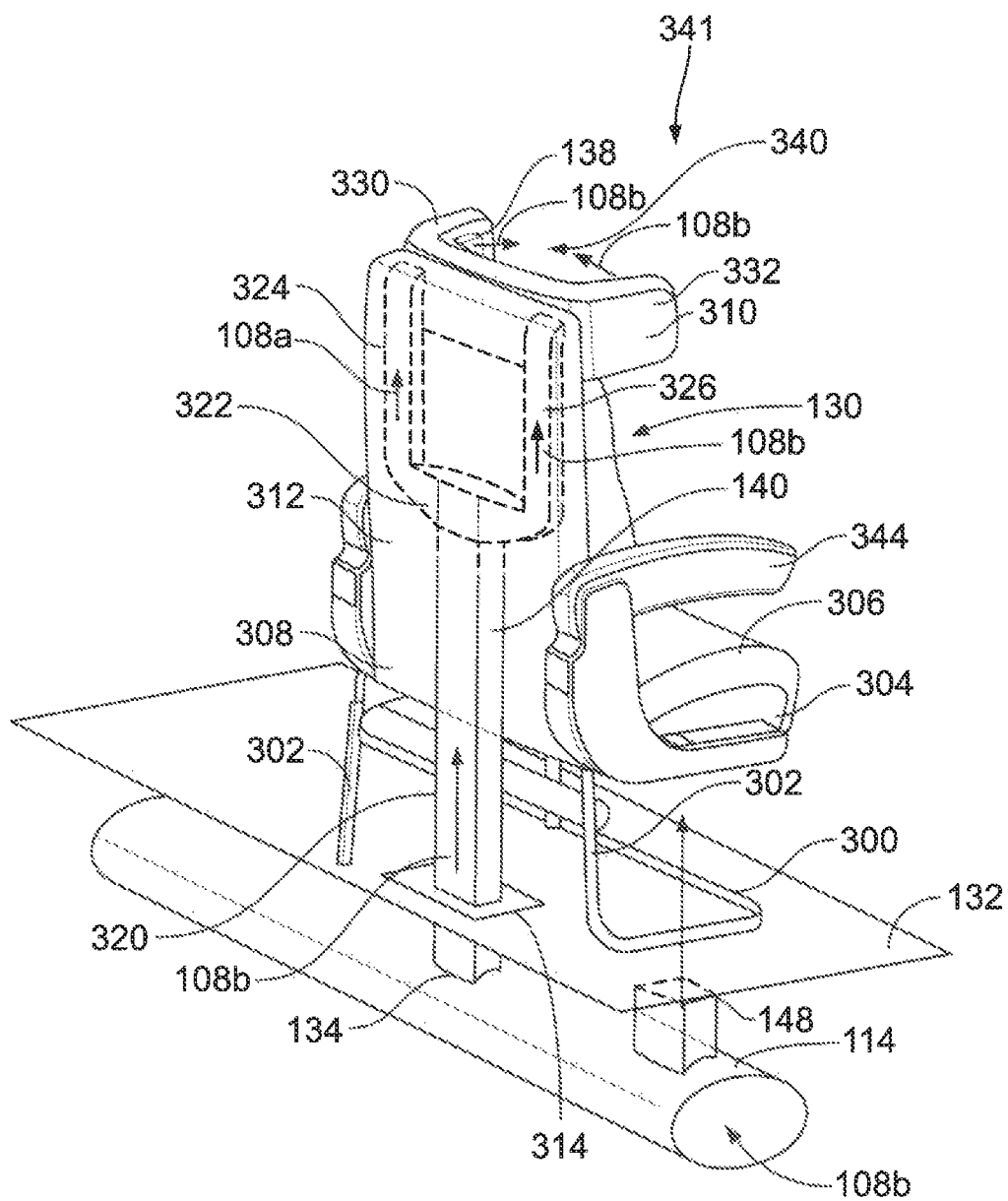
FIG. 5 illustrates a perspective rear view of a seat assembly fluidly coupled to an air delivery manifold, according to an embodiment of the subject disclosure.

FIG. 5 illustrates a perspective rear view of a seat assembly 130 fluidly coupled to the air delivery manifold 114, according to an embodiment of the subject disclosure. The seat assembly 130 includes a base 300, which may include legs 302. The base 300 supports a seat pan 304 having a seat cushion 306. A backrest 308 upwardly extends from a rear of the seat pan 304. A headrest 310 is at an upper portion of the backrest 308.

As shown, the seat duct 140 is secured within and/or to a rear 312 of the backrest 308. The seat duct 140 downwardly extends from the backrest 308, through an opening 314 of the floor 132 and into fluid communication with the outlet port 134 of the air delivery manifold 114.

In at least one embodiment, the seat duct 140 includes a main segment 320 that directly couples to the outlet port 134. The main segment 320 receives the treated air 108b from the air delivery manifold 114. The main segment 320 fluidly connects to a branching segment 322, such as can be disposed inside of the backrest 308. The branching segment 322, in turn, fluid connects to a left segment 324 and a right segment 326. The left segment 324 fluidly connects to air outlets 138 (such as distribution nozzles) of a left wing 330 of the headrest 310. The right segment 324 fluidly connects to air outlets 138 of a right wing 332 of the headrest 310. As such, the air outlets 138 deliver the treated air 108b to either side of a breathing space 340 of the headrest 310.

In at least one embodiment, the breathing space 340 may not extend past lateral or rear portions of the headrest 310. Further, the breathing space 340 may not extend forwardly past a rear surface of a seat assembly (not shown) immediately in front of the seat assembly 130. As such, the breathing space 340 can be confined to a volume of space associated with a seating volume 341 of (that is, the volume of space in which a passenger is seated with respect to) the seat assembly 130. The bottom-up airflow of the treated air 108b delivered to breathing space 340 delivers, fresh, treated air 108b to the breathing space 340, and exhaled air is drawn upwardly into the return air grills 147 (as shown and described with respect to FIG. 1).

The seat duct 140 can be configured differently than shown. For example, the seat duct 140 may not having a branching segment. For example, the seat duct 140 can be fluidly coupled to air outlets 138 on one side of the breathing space 340, over the breathing space, and/or the like. In at least one other embodiment, the seat duct 140 can branch to additional air outlets 138, such as over the breathing space 340 or under the breathing space 340.

In at least one embodiment, the seat assembly 130 may not include the wings 330 and 332. Instead, the air outlets 138 can be disposed on and/or within front and/or rear portions of the headrest 310. In at least one embodiment, the air outlets 138 can be disposed in other portions of the seat assembly 130 in addition to, or in place of, the headrest 310. For example, the air outlets 138 can be disposed on and/or within other portions of the backrest 308, arm rests 344, the base 300, and/or the like. The seat assembly 130 shown in FIG. 5 is merely exemplary, and non-limiting.

Figure 6:
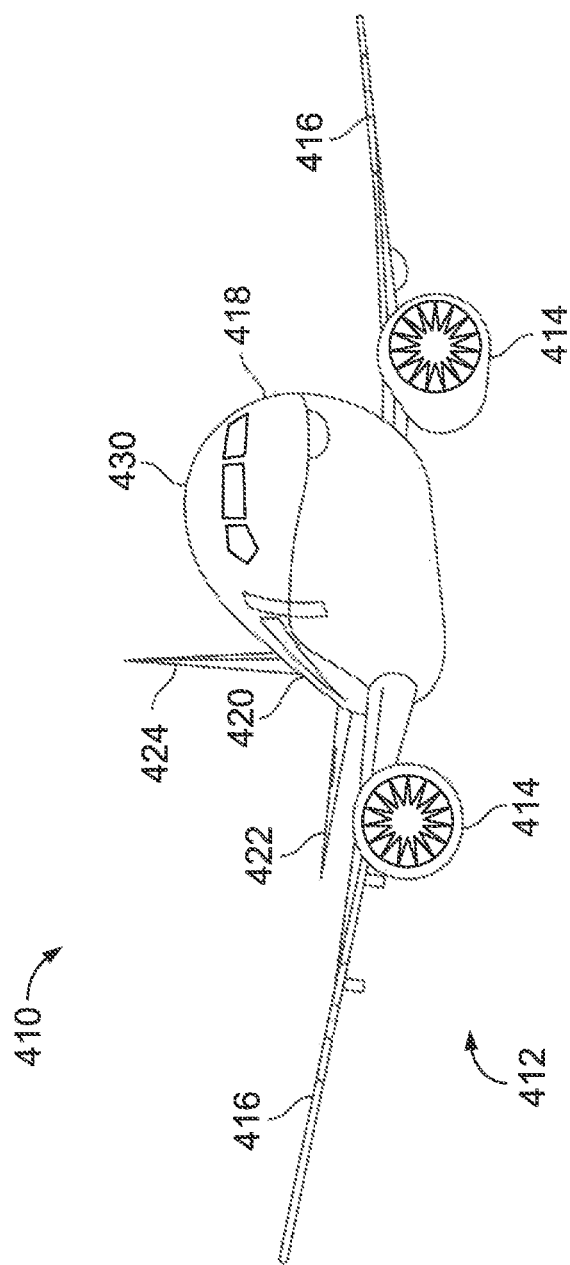
FIG. 6 illustrates a perspective front view of an aircraft, according to an embodiment of the subject disclosure.

FIG. 6 illustrates a perspective front view of an aircraft 410, according to an embodiment of the subject disclosure. The aircraft 410 is an example of the vehicle 102 shown in FIG. 1.

The aircraft 410 includes a propulsion system 412 that includes engines 414, for example. Optionally, the propulsion system 412 can include more engines 414 than shown. The engines 414 are carried by wings 416 of the aircraft 410. In other embodiments, the engines 414 can be carried by a fuselage 418 and/or an empennage 420. The empennage 420 can also support horizontal stabilizers 422 and a vertical stabilizer 424.

The fuselage 418 of the aircraft 410 defines an internal cabin 430, which includes a flight deck or cockpit, one or more work sections (for example, galleys, personnel carry-on baggage areas, and the like), one or more passenger sections (for example, first class, business class, and coach sections), one or more lavatories, and/or the like.

Alternatively, instead of an aircraft, embodiments of the subject disclosure can be used with various other vehicles, such as automobiles, buses, locomotives and train cars, watercraft, and the like. Further, embodiments of the subject disclosure can be used with respect to fixed structures, such as commercial and residential buildings (for example, theaters, concert venues, auditoriums, classrooms, stadiums, grocery stores, office buildings, hospitals, and the like).

Figure 7A:
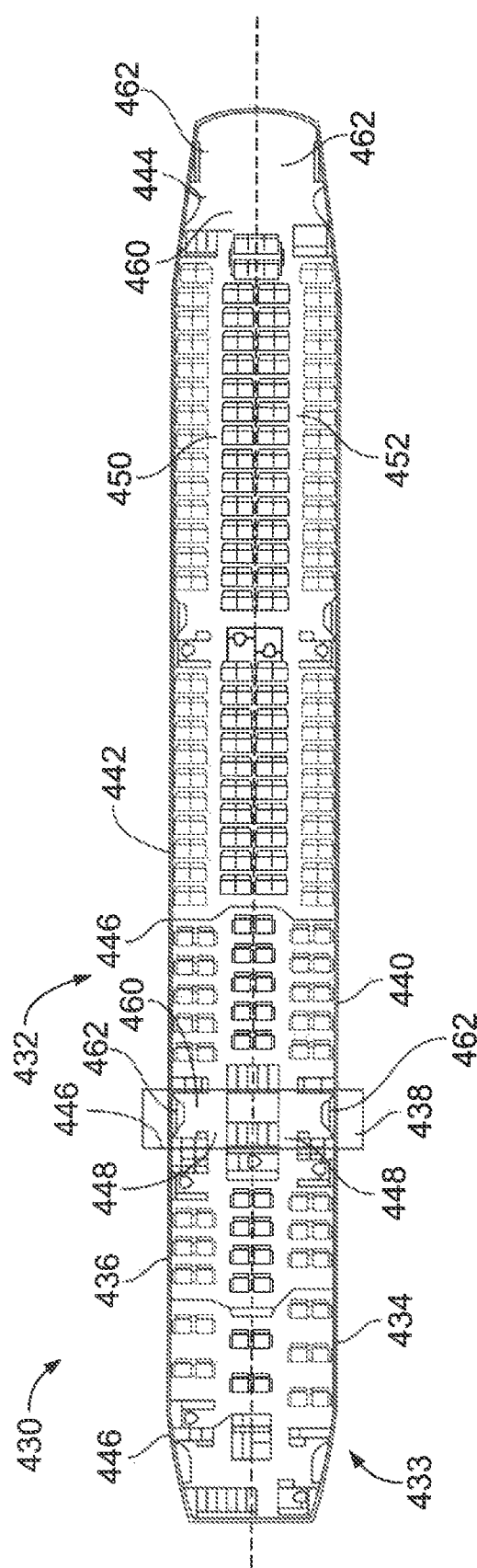
FIG. 7A illustrates a top plan view of an internal cabin of an aircraft, according to an embodiment of the subject disclosure.

FIG. 7A illustrates a top plan view of an internal cabin 430 of an aircraft, according to an embodiment of the subject disclosure. The internal cabin 430 can be within the fuselage 432 of the aircraft, such as the fuselage 418 of FIG. 6. For example, one or more fuselage walls can define the internal cabin 430. The internal cabin 430 includes multiple sections, including a front section 433, a first class section 434, a business class section 436, a front galley station 438, an expanded economy or coach section 440, a standard economy of coach section 442, and an aft section 444, which can include multiple lavatories and galley stations. It is to be understood that the internal cabin 430 can include more or less sections than shown. For example, the internal cabin 430 may not include a first class section, and can include more or less galley stations than shown. Each of the sections can be separated by a cabin transition area 446, which can include class divider assemblies between aisles 448.

As shown in FIG. 7A, the internal cabin 430 includes two aisles 450 and 452 that lead to the aft section 444. Optionally, the internal cabin 430 can have less or more aisles than shown. For example, the internal cabin 430 can include a single aisle that extends through the center of the internal cabin 430 that leads to the aft section 444.

The aisles 448, 450, and 452 extend to egress paths or door passageways 460. Exit doors 462 are located at ends of the egress paths 460. The egress paths 460 can be perpendicular to the aisles 448, 450, and 452. The internal cabin 430 can include more egress paths 460 at different locations than shown. The air distribution system 100 shown and described with respect to FIG. 1, for example, is configured to be used within the internal cabin 430.

Figure 7B:
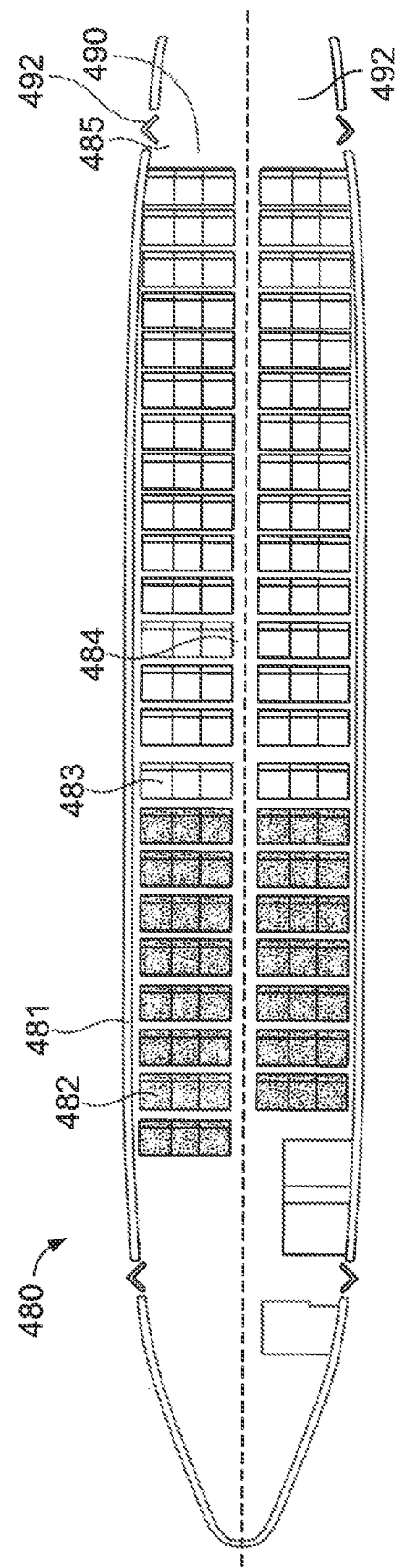
FIG. 7B illustrates a top plan view of an internal cabin of an aircraft, according to an embodiment of the subject disclosure.

FIG. 7B illustrates a top plan view of an internal cabin 480 of an aircraft, according to an embodiment of the subject disclosure. The internal cabin 480 is an example of the internal cabin 430 shown in FIG. 6. The internal cabin 480 can be within a fuselage 481 of the aircraft. For example, one or more fuselage walls can define the internal cabin 480. The internal cabin 480 includes multiple sections, including a main cabin 482 having passenger seats 483, and an aft section 485 behind the main cabin 482. It is to be understood that the internal cabin 480 can include more or less sections than shown.

The internal cabin 480 can include a single aisle 484 that leads to the aft section 485. The single aisle 484 can extend through the center of the internal cabin 480 that leads to the aft section 485. For example, the single aisle 484 can be coaxially aligned with a central longitudinal plane of the internal cabin 480.

The aisle 484 extends to an egress path or door passageway 490. Exit doors 492 are located at ends of the egress path 490. The egress path 490 can be perpendicular to the aisle 484. The internal cabin 480 can include more egress paths than shown. The air distribution system 100 shown and described with respect to FIG. 1, for example, is configured to be used within the internal cabin 480.

Figure 8:
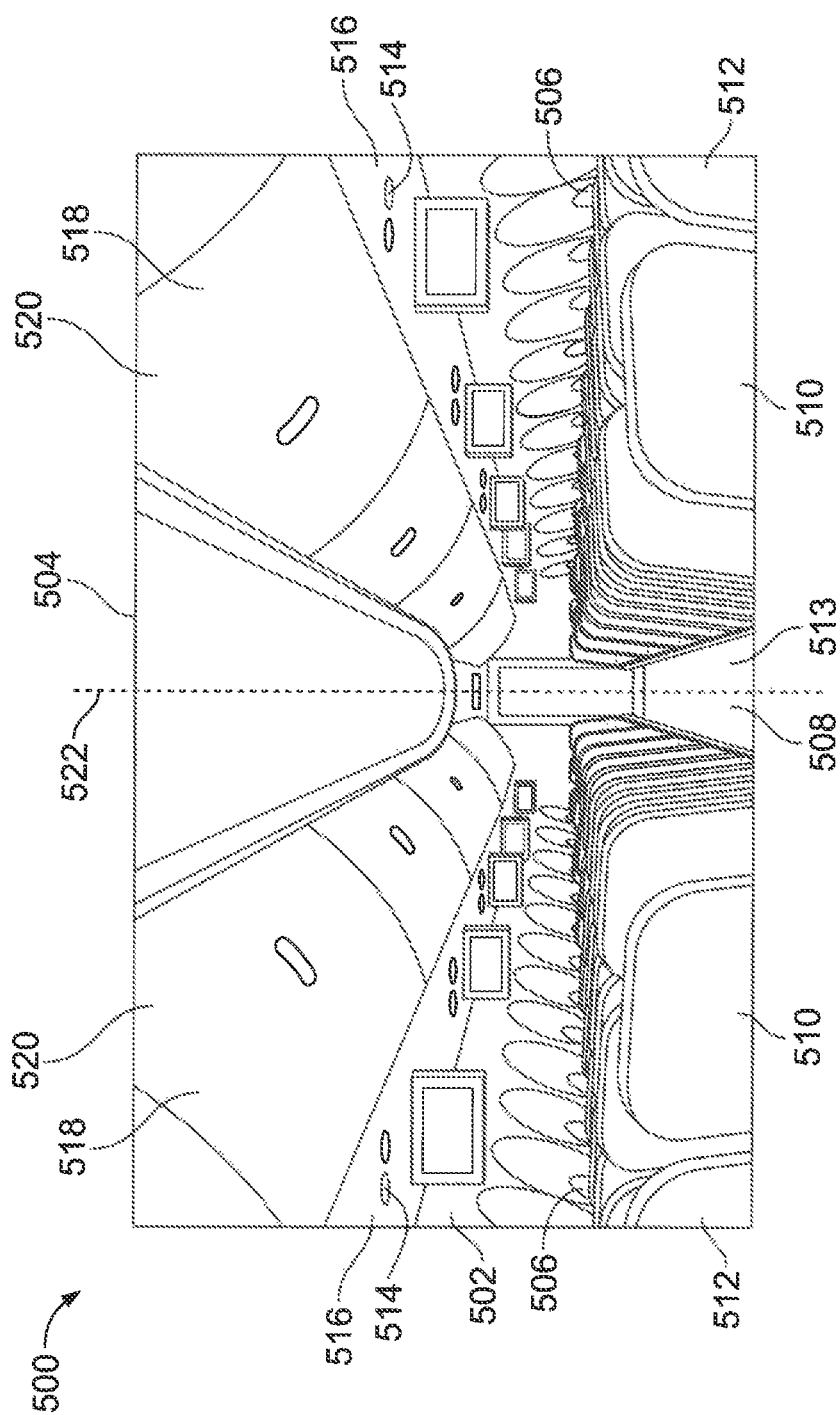
FIG. 8 illustrates a perspective interior view of an internal cabin of an aircraft, according to an embodiment of the subject disclosure.

FIG. 8 illustrates a perspective interior view of an internal cabin 500 of an aircraft, according to an embodiment of the subject disclosure. The internal cabin 500 includes outboard walls 502 connected to a ceiling 504. Windows 506 can be formed within the outboard walls 502. A floor 508 supports rows of seats 510. As shown in FIG. 8, a row 512 can include two seats 510 on either side of an aisle 513. However, the row 512 can include more or less seats 510 than shown. Additionally, the internal cabin 500 can include more aisles than shown.

PSUs 514 are secured between an outboard wall 502 and the ceiling 504 on either side of the aisle 513. The PSUs 514 extend between a front end and rear end of the internal cabin 500. For example, a PSU 514 can be positioned over each seat 510 within a row 512. Each PSU 514 can include a housing 516 that generally contains vents, reading lights, an oxygen bag drop panel, an attendant request button, and other such controls over each seat 510 (or groups of seats) within a row 512.

Overhead stowage bin assemblies 518 are secured to the ceiling 504 and/or the outboard wall 502 above and inboard from the PSU 514 on either side of the aisle 513. The overhead stowage bin assemblies 518 are secured over the seats 510. The overhead stowage bin assemblies 518 extend between the front and rear end of the internal cabin 500. Each stowage bin assembly 518 can include a pivot bin or bucket 520 pivotally secured to a strongback (hidden from view in FIG. 8). The overhead stowage bin assemblies 518 can be positioned above and inboard from lower surfaces of the PSUs 514. The overhead stowage bin assemblies 518 are configured to be pivoted open in order to receive passenger carry-on baggage and personal items, for example.

As used herein, the term "outboard" means a position that is further away from a central longitudinal plane 522 of the internal cabin 500 as compared to another component. The term "inboard" means a position that is closer to the central longitudinal plane 522 of the internal cabin 500 as compared to another component. For example, a lower surface of a PSU 514 can be outboard in relation to a stowage bin assembly 518.

The air distribution system 100 shown and described with respect to FIG. 1, for example, is configured to be used within the internal cabin 500.

Figure 9:
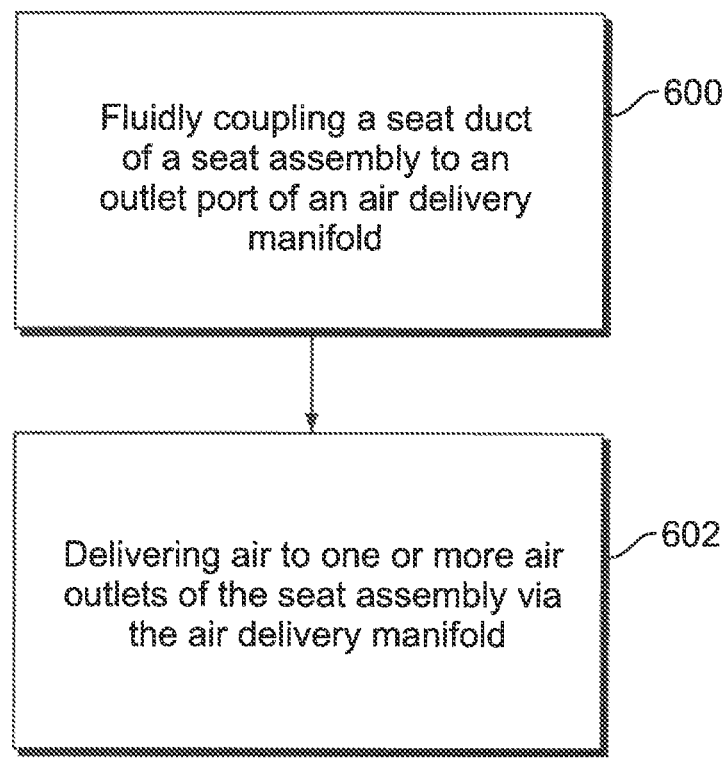
FIG. 9 illustrates a flow chart of an air distribution method, according to an embodiment of the subject disclosure.

FIG. 9 illustrates a flow chart of an air distribution method, according to an embodiment of the subject disclosure. The method includes fluidly coupling, at 600, a seat duct of a seat assembly to a first outlet port of an air delivery manifold underneath the seat assembly; and delivering, at 602, air to one or more air outlets of the seat assembly via the air delivery manifold.

In at least one example, the method also includes receiving the air with an air supply, drawing the air into a supply duct that is fluidly coupled to the air supply and the air delivery manifold, and providing the air to the air delivery manifold from the supply duct.

In at least one example, the method also includes disposing one or more fans disposed within the supply duct.

In at least one example, the method also includes disposing an air conditioning sub-system on or within the supply duct upstream from the air delivery manifold.

In at least one example, the method also includes disposing an ultraviolet (UV) disinfection sub-system on or within the supply duct upstream from the air delivery manifold, and emitting, by one or more UV light emitters of the UV disinfection sub-system, UV light into the air.

In at least one example, the method also includes providing the air into an internal cabin through a second outlet port of the air delivery manifold.

In at least one example, the method also includes disposing one or more return air grills above the seat assembly, and upwardly drawing the air from a breathing space associated with the seat assembly into the one or more return air grills.

In at least one example, the method also includes removably coupling the seat duct to the first outlet port.

As described herein, embodiments of the subject disclosure provide systems and methods for preventing, minimizing, or otherwise reducing the spread of pathogens between passengers onboard a vehicle during a trip, such as between passengers in an internal cabin of an aircraft during a flight, without risking harm to the passengers.

Further, the disclosure comprises embodiments according to the following clauses:

Clause 1. A system comprising:
a seat assembly comprising a seat duct fluidly coupled to one or more air outlets; and
an air delivery manifold underneath the seat assembly, wherein the air delivery manifold comprises a first outlet port, wherein the seat duct is fluidly coupled to the first outlet port, and wherein air is to be delivered to the one or more air outlets via the air delivery manifold.

Clause 2. The system of Clause 1, wherein the air delivery manifold is below a floor, and wherein the seat assembly is supported on a top surface of the floor.

Clause 3. The system of Clauses 1 or 2, further comprising:
an air supply that receives the air; and
a supply duct fluidly coupled to the air supply and the air delivery manifold, wherein the air is drawn into the supply duct from the air supply and provided to the air delivery manifold from the supply duct.

Clause 4. The system of Clause 3, further comprising one or more fans disposed within the supply duct.

Clause 5. The system of Clauses 3 or 4, further comprising an air conditioning sub-system disposed on or within the supply duct upstream from the air delivery manifold.

Clause 6. The system of Clause 5, wherein the air conditioning sub-system comprises at least one of one or more heaters, one or more filters, or one or more humidifiers.

Clause 7. The system of any of Clauses 3-6, further comprising an ultraviolet (UV) disinfection sub-system disposed on or within the supply duct upstream from the air delivery manifold, wherein the UV disinfection sub-system comprises one or more UV light emitters configured to emit UV light into the air.

Clause 8. The system of any of Clauses 1-7, wherein the air delivery manifold further comprises a second outlet port.

Clause 9. The system of Clause 8, wherein the second outlet port is open and configured to provide the air into an internal cabin.

Clause 10. The system of Clauses 8 or 9, wherein the second outlet port is plugged.

Clause 11. The system of any of clauses 1-10, wherein at least a portion of the seat duct extends into at least a portion of one or both of a backrest or a headrest of the seat assembly.

Clause 12. The system of Clause 11, wherein the headrest includes the one or more air outlets.

Clause 13. The system of any of Clauses 1-12, further comprising one or more return air grills above the seat assembly, wherein the air is upwardly drawn from a breathing space associated with the seat assembly into the one or more return air grills.

Clause 14. The system of Clause 13, wherein the one or more return air grills are disposed within a ceiling of an internal cabin.

Clause 15. The system of any of Clauses 1-14, wherein the seat duct is removably coupled to the first outlet port.

Clause 16. A method comprising:
fluidly coupling a seat duct of a seat assembly to a first outlet port of an air delivery manifold underneath the seat assembly; and
delivering air to one or more air outlets of the seat assembly via the air delivery manifold.

Clause 17. The method of Clause 16, wherein the air delivery manifold is below a floor, and wherein the seat assembly is supported on a top surface of the floor.

Clause 18. The method of Clauses 16 or 17, further comprising:
receiving air with an air supply;
drawing the air into a supply duct that is fluidly coupled to the air supply and the air delivery manifold; and
providing the air to the air delivery manifold from the supply duct.

Clause 19. The method of Clause 18, further comprising disposing one or more fans disposed within the supply duct.

Clause 20. The method of Clauses 18 or 19, further comprising disposing an air conditioning sub-system on or within the supply duct upstream from the air delivery manifold.

Clause 21. The method of any of Clauses 18-20, further comprising:
 disposing an ultraviolet (UV) disinfection sub-system on or within the supply duct upstream from the air delivery manifold; and
 emitting, by one or more UV light emitters of the UV disinfection sub-system, UV light into the air.

Clause 22. The method any of Clauses 16-21, further comprising providing the air into an internal cabin through a second outlet port of the air delivery manifold.

Clause 23. The method of any of Clauses 16-22, further comprising:
 disposing one or more return air grills above the seat assembly; and
 upwardly drawing the air from a breathing space associated with the seat assembly into the one or more return air grills.

Clause 24. The method of any of Clauses 16-23, further comprising removably coupling the seat duct to the first outlet port.

Clause 25. A vehicle comprising:
 an interior cabin including a floor;
 a seat assembly supported on a top surface of the floor within the interior cabin, wherein the seat assembly includes a seat duct fluidly coupled to one or more air outlets; and
 an air delivery manifold below the floor underneath the seat assembly, wherein the air delivery manifold comprises a first outlet port, wherein the seat duct is fluidly coupled to the first outlet port, and wherein air is delivered to the one or more air outlets via the air delivery manifold.
 an air supply that receives air;
 a supply duct fluidly coupled to the air supply and the air delivery manifold, wherein the air is drawn into the supply duct from the air supply and provided to the air delivery manifold from the supply duct.
 one or more fans disposed within the supply duct;
 an air conditioning sub-system disposed on or within the supply duct upstream from the air delivery manifold;
 an ultraviolet (UV) disinfection sub-system disposed on or within the supply duct upstream from the air delivery manifold, wherein the UV disinfection sub-system comprises one or more UV light emitters configured to emit UV light into the air; and
 one or more return air grills above the seat assembly, wherein the air is upwardly drawn from a breathing space associated with the seat assembly into the one or more return air grills.

While various spatial and directional terms, such as top, bottom, lower, mid, lateral, horizontal, vertical, front and the like can be used to describe embodiments of the subject disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "containing" are used as the plain-English equivalents of the term "comprising" and the term "in which" is used as the plain-English equivalents of the term "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system comprising:
 a seat assembly comprising a backrest, a headrest, and a seat duct fluidly coupled to one or more air outlets, wherein the seat duct includes one of a plug or a socket, wherein the seat duct is within or on a rear of the backrest, and wherein the seat duct downwardly extends from the backrest;
 an air delivery manifold underneath the seat assembly, wherein the air delivery manifold comprises a first outlet port including the other of the plug or the socket, wherein the plug connects to the socket to fluidly connect the seat duct to the first outlet port, and wherein air is to be delivered to the one or more air outlets via the air delivery manifold;
 one or more return air grills above the seat assembly, wherein the air is upwardly drawn from a breathing space associated with the seat assembly into the one or more return air grills;
 an air supply that receives the air;
 a supply duct fluidly coupled to the air supply and the air delivery manifold, wherein the air is drawn into the supply duct from the air supply and provided to the air delivery manifold from the supply duct; and
 an ultraviolet (UV) disinfection sub-system disposed on or within the supply duct, wherein the UV disinfection sub-system comprises UV light emitters configured to emit UV light into the air, and wherein the UV light emitters are disposed along a length of the supply duct.

2. The system of claim 1, wherein the air delivery manifold is below a floor, wherein the seat assembly is supported on a top surface of the floor, and wherein the seat duct downwardly extends from the backrest through an opening in the floor.

3. The system of claim 1, further comprising one or more fans disposed within the supply duct.

4. The system of claim 1, further comprising an air conditioning sub-system disposed on or within the supply duct upstream from the air delivery manifold.

5. The system of claim 4, wherein the air conditioning sub-system comprises at least one of one or more heaters, one or more filters, or one or more humidifiers.

6. The system of claim 1, wherein the air delivery manifold further comprises a second outlet port.

7. The system of claim 6, wherein the second outlet port is open and configured to provide the air into an internal cabin.

8. The system of claim 6, wherein the second outlet port is plugged.

9. The system of claim 1, wherein at least a portion of the seat duct extends into at least a portion of one or both of the backrest or the headrest of the seat assembly.

10. The system of claim 9, wherein the headrest comprises a left wing having left air outlets, and a right wing having right air outlets, wherein the one or more air outlets comprise the left air outlets and the right air outlets, and wherein the seat duct comprises:
 a main segment directly coupled to the first outlet port;
 a branching segment disposed inside of the backrest, wherein the main segment fluidly connects to the branching segment;
 a left segment fluidly connected to the branching segment and the left air outlets; and
 a right segment fluidly connected to the branching segment and the right air outlets.

11. The system of claim 1, wherein the one or more return air grills are disposed within a ceiling of an internal cabin.

12. The system of claim 1, wherein the seat duct is removably coupled to the first outlet port.

13. A method comprising:
 fluidly coupling a seat duct within or on a rear of a backrest of a seat assembly to a first outlet port of an air delivery manifold underneath the seat assembly, wherein the seat duct downwardly extends from the backrest, wherein said fluidly coupling comprises connecting one of a plug or a socket of the seat duct to the other of the plug or the like of the first outlet port;
 delivering air to one or more air outlets of the seat assembly via the air delivery manifold;
 disposing one or more return air grills above the seat assembly;
 upwardly drawing the air from a breathing space associated with the seat assembly into the one or more return air grills;
 receiving the air with an air supply;
 drawing the air into a supply duct that is fluidly coupled to the air supply and the air delivery manifold;
 providing the air to the air delivery manifold from the supply duct; and
 disposing an ultraviolet (UV) disinfection sub-system on or within the supply duct upstream from the air delivery manifold, wherein UV light emitters of the UV disinfection sub-system emit UV light into the air, and wherein said disposing the UV disinfection sub-system comprises disposing the UV light emitters along a length of the supply duct.

14. The method of claim 13, wherein the air delivery manifold is below a floor, wherein the seat assembly is supported on a top surface of the floor, and wherein the seat duct downwardly extends from the backrest through an opening in the floor.

15. The method of claim 13, further comprising disposing:
 one or more fans disposed within the supply duct; and
 an air conditioning sub-system on or within the supply duct upstream from the air delivery manifold.

16. The method of claim 13, further comprising providing the air into an internal cabin through a second outlet port of the air delivery manifold.

17. The method of claim 13, further comprising removably coupling the seat duct to the first outlet port.

18. The method of claim 13, wherein the one or more return air grills are disposed within a ceiling of an internal cabin.

19. A system comprising:
 a seat assembly configured to be supported on a top surface of a floor within an interior cabin, wherein the seat assembly includes a backrest, a headrest, and a seat duct fluidly coupled to one or more air outlets, wherein the seat duct includes one of a plug or a socket, wherein the seat duct is within or on a rear of the backrest, and wherein the seat duct downwardly extends from the backrest;
 an air delivery manifold configured to be below the floor underneath the seat assembly, wherein the air delivery manifold comprises a first outlet port including the other of the plug or the socket, wherein the plug connects to the socket to fluidly connect the seat duct to the first outlet port, and wherein air is delivered to the one or more air outlets via the air delivery manifold;
 an air supply that receives the air;
 a supply duct fluidly coupled to the air supply and the air delivery manifold, wherein the air is drawn into the supply duct from the air supply and provided to the air delivery manifold from the supply duct;
 one or more fans disposed within the supply duct;
 an air conditioning sub-system disposed on or within the supply duct upstream from the air delivery manifold;
 an ultraviolet (UV) disinfection sub-system disposed on or within the supply duct upstream from the air delivery manifold, wherein the UV disinfection sub-system comprises UV light emitters configured to emit UV light into the air, and wherein the UV light emitters are disposed along a length of the supply duct; and
 one or more return air grills above the seat assembly, wherein the air is upwardly drawn from a breathing space associated with the seat assembly into the one or more return air grills.

20. A system comprising:
 a seat assembly comprising a backrest, a headrest, and a seat duct fluidly coupled to one or more air outlets, wherein the seat duct includes one of a plug or a socket, wherein the seat duct is within or on a rear of the backrest, wherein the seat duct downwardly extends from the backrest, wherein at least a portion of the seat duct extends into at least a portion of one or both of the backrest or the headrest of the seat assembly, wherein the headrest comprises a left wing having left air outlets, and a right wing having right air outlets, wherein the one or more air outlets comprise the left air outlets and the right air outlets, and wherein the seat duct comprises:
- a main segment directly coupled to the first outlet port;
- a branching segment disposed inside of the backrest, wherein the main segment fluidly connects to the branching segment;
- a left segment fluidly connected to the branching segment and the left air outlets; and
- a right segment fluidly connected to the branching segment and the right air outlets;

an air delivery manifold underneath the seat assembly, wherein the air delivery manifold comprises a first outlet port including the other of the plug or the socket, wherein the plug connects to the socket to fluidly connect the seat duct to the first outlet port, and wherein air is to be delivered to the one or more air outlets via the air delivery manifold;

an air supply that receives the air;

a supply duct fluidly coupled to the air supply and the air delivery manifold, wherein the air is drawn into the supply duct from the air supply and provided to the air delivery manifold from the supply duct; and an ultraviolet (UV) disinfection sub-system disposed on or within the supply duct, wherein the UV disinfection sub-system comprises UV light emitters configured to emit UV light into the air, and wherein the UV light emitters are disposed along a length of the supply duct.

* * * * *